(12) United States Patent
Agurok

(10) Patent No.: US 8,939,579 B2
(45) Date of Patent: Jan. 27, 2015

(54) AUTOFOCUSING EYEWEAR, ESPECIALLY FOR PRESBYOPIA CORRECTION

(75) Inventor: Ilya Agurok, Santa Clarita, CA (US)

(73) Assignee: Light Prescriptions Innovators, LLC, Altadena, CA (US)

(*) Notice: Subject to any disclaimer, the term of this patent is extended or adjusted under 35 U.S.C. 154(b) by 266 days.

(21) Appl. No.: 13/358,904

(22) Filed: Jan. 26, 2012

(65) Prior Publication Data

US 2012/0194781 A1 Aug. 2, 2012

Related U.S. Application Data

(60) Provisional application No. 61/437,183, filed on Jan. 28, 2011, provisional application No. 61/627,213, filed on Oct. 7, 2011.

(51) Int. Cl.
*A61B 3/08* (2006.01)
*A61B 3/10* (2006.01)
*G02C 7/08* (2006.01)
*A61B 3/113* (2006.01)

(52) U.S. Cl.
CPC .............. *G02C 7/081* (2013.01); *A61B 3/113* (2013.01)
USPC .......................................... 351/205; 351/201

(58) Field of Classification Search
USPC .......................................... 351/201–204, 224
See application file for complete search history.

(56) References Cited

U.S. PATENT DOCUMENTS

| 2004/0032567 | A1* | 2/2004 | Fukuma et al. | 351/228 |
| 2010/0045933 | A1* | 2/2010 | Eberl et al. | 351/210 |
| 2010/0220288 | A1* | 9/2010 | Cleveland | 351/206 |
| 2011/0043644 | A1* | 2/2011 | Munger et al. | 348/207.1 |
| 2011/0228226 | A1* | 9/2011 | Pixton et al. | 351/222 |

* cited by examiner

*Primary Examiner* — Mahidere Sahle
(74) *Attorney, Agent, or Firm* — Drinker Biddle & Reath LLP

(57) ABSTRACT

A pair of eyewear has transparent waveguides in each eyewear lens. An illumination subsystem directs a beam of light through the waveguides onto a wearer's eyes. A First Purkinje point imaging subsystem for each lens uses light reflected from the eyes through the waveguides. A controller calculates from the positions of the First Purkinje points the wearer's gaze parallax angle and/or the distance to an object of interest on which the gaze of the wearer's eyes converges. The output of the controller may drive variable-focus eyeglass lenses to enable a presbyopic wearer to focus on the object. Modified Alvarez variable-focus lenses are described.

13 Claims, 14 Drawing Sheets

AUTOFOCUSING EYEWEAR, ESPECIALLY FOR PRESBYOPIA CORRECTION

CROSS REFERENCE TO RELATED APPLICATIONS

This application claims benefit of U.S. Provisional Patent Application No. 61/437,183, filed Jan. 28, 2011 by Agurok, and of U.S. Provisional Patent Application No. 61/627,213, filed Oct. 7, 2011 by Agurok, both of which applications are incorporated herein by reference in their entirety.

This application makes reference to U.S. Pat. No. 3,305,294, issued Feb. 21, 1967 to Alvarez, which is incorporated herein by reference in its entirety.

BACKGROUND OF THE INVENTION

Presbyopia is a condition where the eye has diminished ability to focus on near objects, a so-called reduction in the ability of the eye to "accommodate" (change the shape of the lens). Usually presbyopia progressively gets worse after a certain age of an individual, typically starting after the age of 40. Young children nearly all have the ability to focus their eyes from infinity down to as close as a distance of 50 mm, after correction for any far or near sight (20 diopters of optical power). However, by the age of 50 the average person can only accommodate their eyes by 2 diopters, a ten to one reduction.

U.S. Pat. No. 3,305,294, issued Feb. 21, 1967 to Alvarez, Ref. [5], which is incorporated herein by reference in its entirety, describes a two-element variable-power spherical lens in which the two elements slide across each other to vary the power. That lens is referred to below as an "Alvarez lens."

Recently PixelOptics Corp. (www.pixeloptics.com) has developed glasses that can allow a user to switch focus from their far distance prescription to their prescription for reading. This is accomplished using a Liquid Crystal modulator made by the Panasonic Healthcare Company. Devices having continuous focusing ability include: Superfocus (www.superfocus.com) and Adlens (www.adlens.com), which manufacture eyeglasses that employ a flexible membrane lens; Centre for Vision in the Developing World (www.vdwoxford.com) that manufactures glasses that employ an Alvarez lens; and Eyejusters (www.eyejusters.com), who also use an Alvarez lens. In order for such devices to work properly, and to automatically adjust the prescription commensurate with the task, some type of driving signal must be obtained from the user. All of the above mentioned companies are supplying glasses with an adjustment knob, hardly an automatic system. Such an approach is cumbersome, especially when the user has both hands busy, such as in a driving situation. A more recent model from PixelOptics is activated by changes in the output of an accelerometer when the user changes the position of his or her head (head faces downward when the reading glasses prescription is required). However, basing the switch of prescription on moving one's head downward may be appropriate for reading but inappropriate for many other common situations. For example, in the case where someone is walking down a staircase, looking downward, the refocusing of glasses might result in a loss of orientation and potentially incurring an injury. A more reliable way is to monitor the eye parallax, which provides sufficient information to determine the distance to the intended object and therefore of the task at hand.

Distance accommodation in human vision is associated with two mutually connected processes: eye focusing and stereovision. In close distance accommodation, the human eye rotates to target such that the axis of each eye is aimed at the object. The angle between these two axes is the parallax angle. The closer the distance of an object the larger the parallax angle associated with the object. Fortunately, the parallax angle can be monitored and determined by using an eye tracking technique. The data from the eye tracker can provide the required signal to properly control the autofocusing device on the eyewear. There are four main approaches presently used for eye tracking: Electro-OculoGraphy (EOG), scleral contact lens/search, Video-OculoGraphy (VOG), and the video-based combined pupil and corneal reflection technique. See Ref. [1].

The EOG technique relies on the measurement of the skin's electric potential differences, using electrodes placed around both eyes. The scleral technique uses special contact lenses with an embedded coil. These techniques are too cumbersome for the typical user of the proposed autofocusing eyewear.

VOG is based on recording of an image of the corneal limbus, and can potentially be designed as a compact device. Nevertheless this technique requires the mounting of two imaging cameras in front of the eyes, either above or below each limbus (just outside of a person's direct view). The presence of such attachments would be uncomfortable and severely limit the number of uses of the eyewear. In addition, when the eye changes its direction of gaze, the limbus image is severely deformed and sophisticated post processing is required to determine the direction of gaze based on the image. This post processing would result in a delay in the response of the eyewear and also the system would likely be plagued by low accuracy.

A video-based system that combines the techniques of pupil reflection and corneal reflection can be more accurate than any of the previously described approaches. In this technique the eye is illuminated by a collimated near-infrared beam. See Refs. [1, 2]. The positions of bright pupil image and the corneal reflection (first Purkinje point) provide sufficient information to determine the direction of the eye gaze. The first Purkinje point is defined as the virtual primary focus of the front surface of the cornea, treated as a convex mirror, with respect to collimated light incident from a direction straight in front of the head of the subject. The first Purkinje point is typically located at 3.875 mm behind the cornea. The line connecting the Purkinje point and the center of the eye pupil is the actual eye axis, which is in fact the gaze direction. Measuring the mutual pupil center and corneal reflex position is a direct method for measuring the direction of gaze. This approach can be performed very quickly and promises higher accuracy than the other approaches. Unfortunately, contemporary cornea/pupil reflection measurement devices are bulky and cannot be efficiently integrated into the autofocusing eyewear. See Ref. [2]. In addition, the eyewear needs only the parallax data, which is the angle between the two gaze directions. The autofocusing eyewear does not need the data regarding the absolute directions of the gaze of each eye, only the angle between the two directions.

What is needed is autofocusing eyewear that is compact and that has a real time parallax measuring subsystem. This subsystem must operate without the use of cumbersome optical attachments that restrict a user's field of view. Also, the subsystem must be lightweight. In this application a new type of autofocus eyewear is revealed and a practical eyetracking subsystem is taught that can meet all the above requirements. This is accomplished through the use of an eyewear integrated holographic infrared light illuminator and a Purkinje points imaging system, neither of which is perceived by the user.

SUMMARY OF THE INVENTION

One aspect of the present invention is related to presbyopia correcting autofocusing eyewear, and to an eye parallax tracker and a variable focus lens suitable for use in such eyewear. The eyewear comprises a controller, an integrated eye parallax tracker and a variable focus eyeglass lens connected in a closed loop system. Unlike prior art gaze tracking systems (that use either the First or Fourth Purkinje imaging points, Ref. [2], or the First Purkinje point and imaging of the limbus, Ref. [1]), which are bulky, embodiments of the present eyewear use images of the First Purkinje point for both eyes to allow a lightweight and compact system.

The parallax tracking system comprises two subsystems: illumination and First Purkinje points imaging. In an embodiment, the two subsystems are interfaced at the lateral edges of the eye-glasses lenses through a beamsplitter. The illumination subsystem may comprise a near-infrared laser diode and collimating optics. Collimated near-infrared light is directed into each lens of the eyewear, or into an associated waveguide. The beam propagates through the lens by total internal reflection. A volume reflection hologram (VRH) is laminated into each of the two lenses of the eyewear at a position opposite the eyes of the wearer. The volume hologram redirects the collimated beam out of the eyewear lens and into the eye.

The reflection from the cornea creates the First Purkinje point. The reflected beam of light from the cornea reaches the VRH and is redirected inside the eyewear lens at an angle that allows total internal reflection. The beam propagates inside the lens and decouples at its lateral edge. Specially designed optics are proximate and receive the ejected light from the eyeglass lens. The optics are designed to compensate the aberrations of the VRH. A microprojection system images the First Purkinje point onto a sensor such as a compact (¼ inch, 6 mm) CCD or PSD. The mutual shift between images of the Purkinje points is proportional to the gaze convergence angle. The system controller calculates the distance to the object of interest and generates the driving signal for the eyewear autofocusing system, based on this gaze convergence angle.

In an embodiment, the variable focus lens is a modified Alvarez lens in which the two components have different optical prescriptions.

BRIEF DESCRIPTION OF THE DRAWINGS

The above and other aspects, features and advantages of the present invention will be apparent from the following more particular description of certain embodiments thereof, presented in conjunction with the following drawings wherein.

DETAILED DESCRIPTION OF PREFERRED EMBODIMENTS

Figure 1:
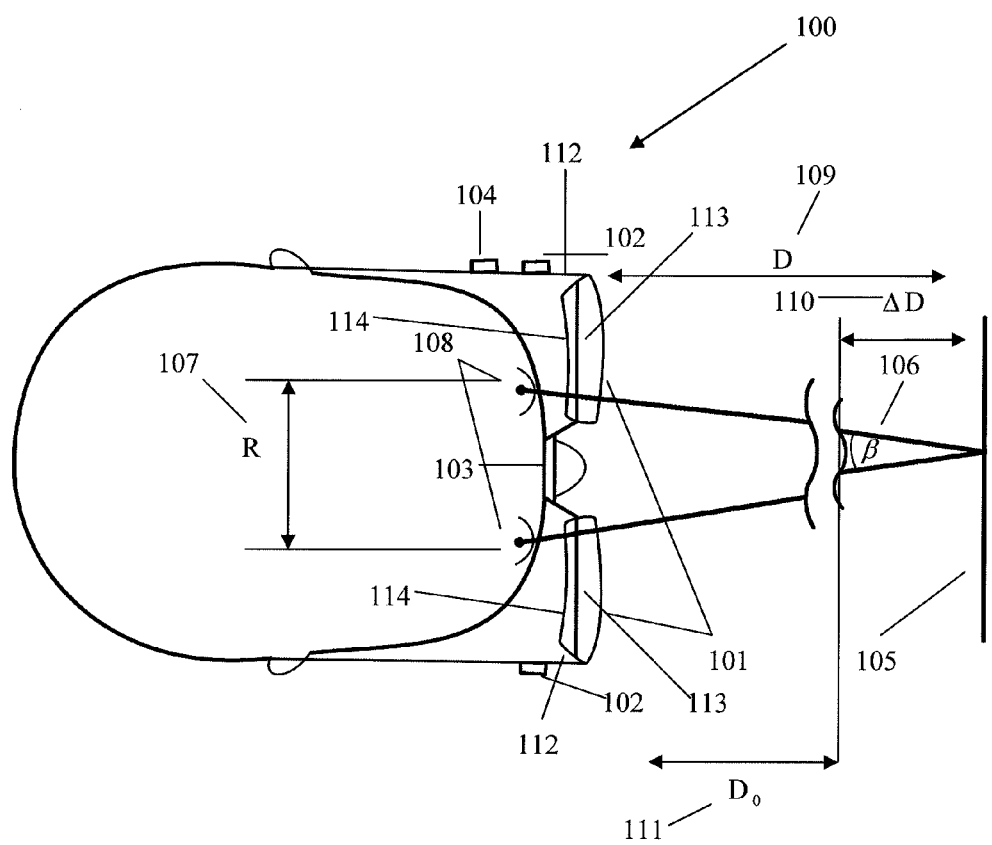
FIG. 1 is a schematic diagram of an embodiment of autofocusing eyewear suitable for presbyopia correction.

FIG. 1 is a schematic diagram that illustrates the functionality of an embodiment of autofocusing presbyopia correcting eyewear, indicated generally by reference numeral 100. In eyewear 100 there are two eyeglass optics 101, each comprising a variable power lens 113 and a gaze tracker waveguide 114. The gaze tracker waveguide 114 has a volume reflection hologram for redirecting a gaze tracker illumination beam from waveguide to the eye as well as redirecting cornea reflex back to the waveguide. Also in FIG. 1 is eye parallax tracker electronics 102. The eye parallax tracker has a cornea illumination system, a cornea reflex imager and a controller 104. The autofocusing eyewear described herein has a variable focus lens driver 103 and a system controller 104. An object plane 105 is at distance 109 (D). When the user concentrates his or her gaze on an object in object plane 105, the lines of gaze for the left and right eyes define parallax angle β 106 and distance R 107 between cornea reflections (the distance between First Purkinje points 108).

Controller 104 may be conventional, comprising a processor, non-volatile storage for programs, programmable non-volatile storage for configuration data, including configuration to the individual user, and volatile storage for working data. Controller 104 may be partially or wholly separated into two controllers, for the eye parallax tracker and for the variable focus lens controller, or may be a single unit. In the interests of simplicity, details of controller 104 are not shown in FIG. 1.

Figure 4:
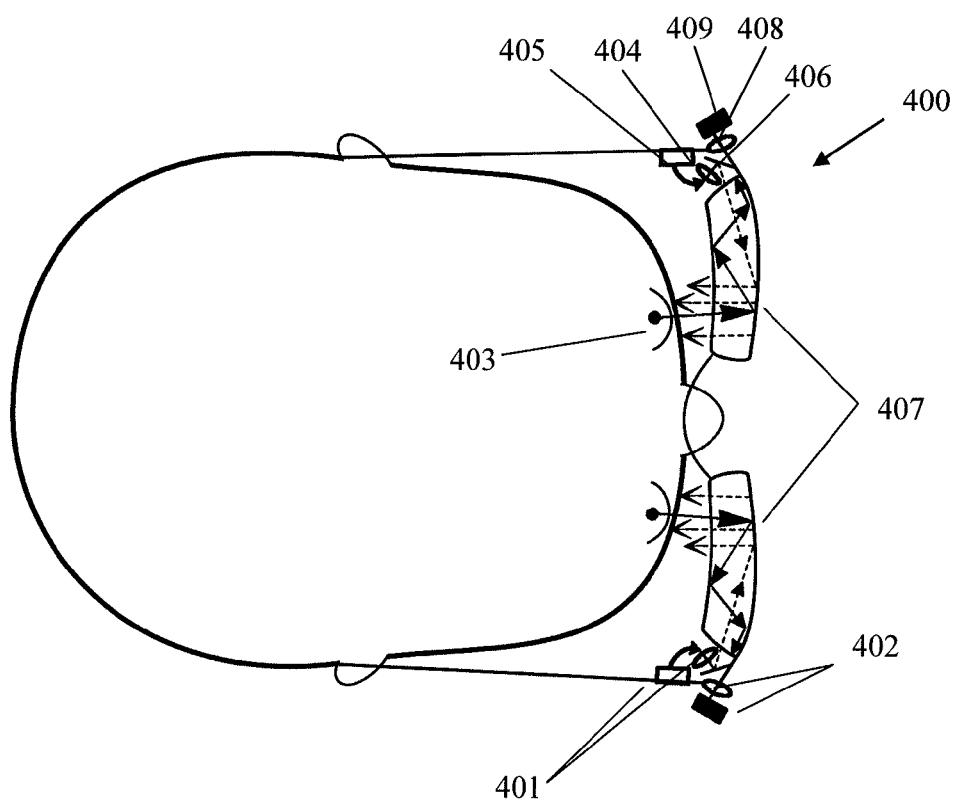
FIG. 4 is a schematic diagram of an embodiment of eyewear integrated gaze tracker.
Figure 6:
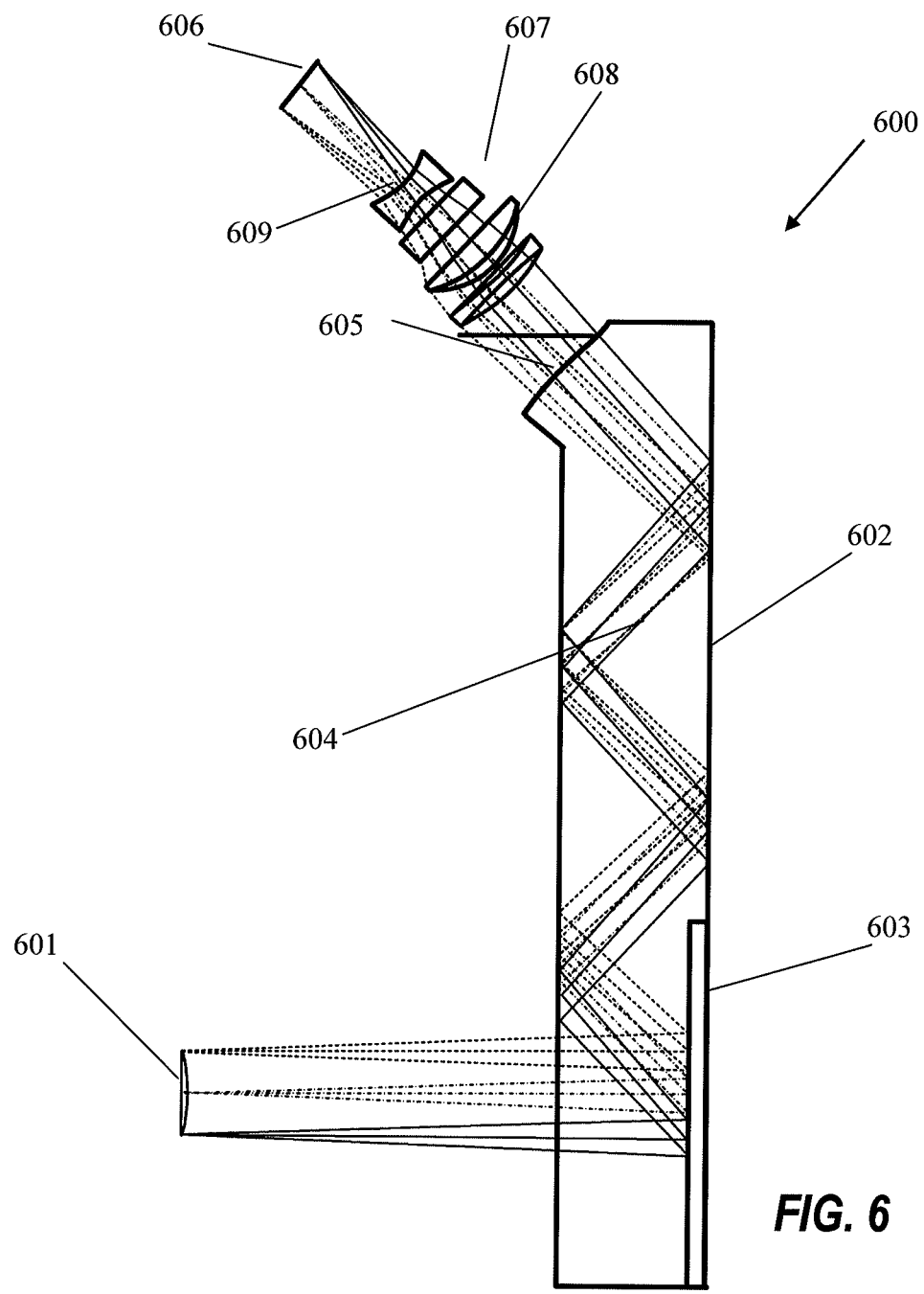
FIG. 6 is an optical layout of a preferred embodiment of an imaging subsystem of an eyewear integrated gaze tracker.

The volume reflection hologram, which is integrated into eyewear visor optics 101, redirects the cornea reflex into visor 112 and a compact microprojection lens images the First Purkinje point onto a receiver (see FIGS. 4 and 6). Microprojection lenses and receivers are located close to the eyewear visor edges 112 and are not shown in FIG. 1. The eye parallax tracker electronics 102 detects the image positions and transfers them to system controller 104. System controller 104 calculates the distance R 107. From distance R, electronics 102 calculates the parallax angle β 106 and the distance D 109 to the object. By knowing the focusing distance D, system controller 104 calculates the refocusing distance ΔD 110, which is the distance between object plane 105 and the individual user's distance for comfortable vision $D_0$ 111. The comfortable vision distance 111 should be determined for each individual and this data programmed into controller 104.

Controller 104 provides a drive signal to variable lens driver 103, based on the calculated values of focusing distance D and refocusing distance ΔD. Driver 103 generates an analog signal for driving the mechanisms that control the variable power lenses, which are integrated into autofocusing glasses optics 101. As soon as the user changes his or her object of attention, the focusing cycle is repeated. Thus, the autofocusing eyewear can enable a person to comfortably read a book even if the reader slightly changes the distance to the book. It can allow a person who is driving to easily switch his or her attention from the road to the dash board and back, with perfect image clarity.

Figure 2:
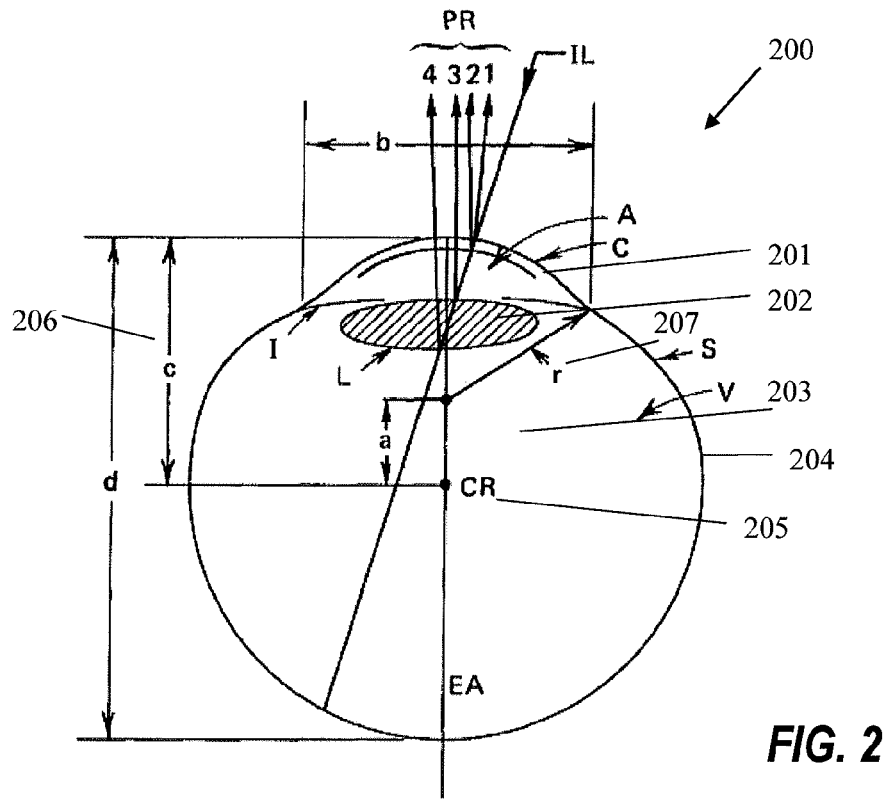
FIG. 2 is a schematic diagram of an average adult human eye.
Figure 3A:
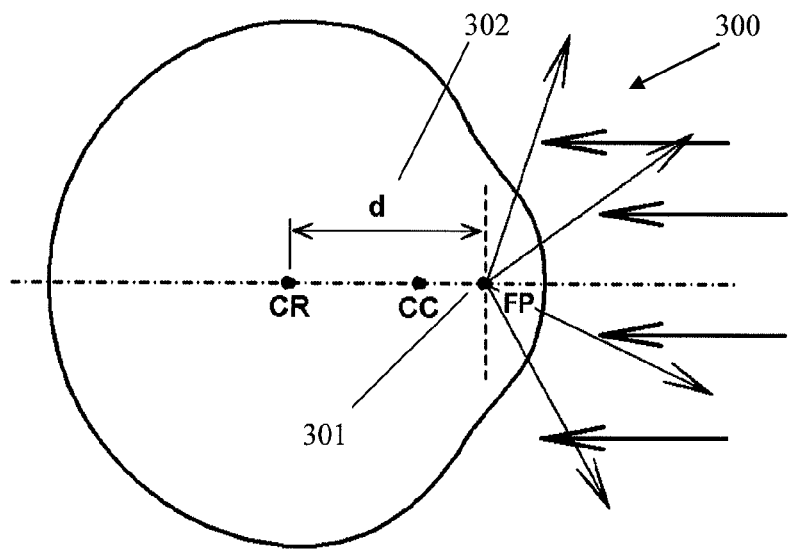
FIG. 3A is a schematic drawing of the reflection of a collimated beam from the cornea of an eye.
Figure 3B:
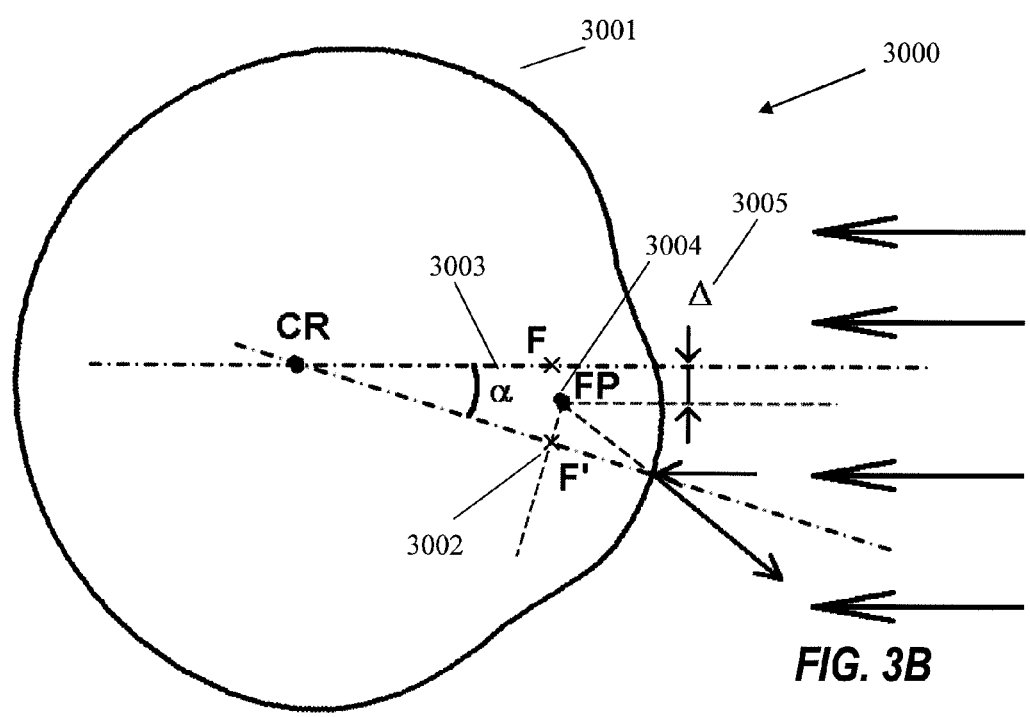
FIG. 3B is a schematic diagram of the changing position of the First Purkinje point as a function of the rotation of the eye.

A schematic diagram of average human eye 200 is shown in FIG. 2. FIG. 2 shows cornea 201, eye lens 202, vitreous 203, and sclera 204. The eye rotates around point 205 (CR) when it gazes at an object of interest. Cornea 201 defines an arc segment C of radius r 207. The distance 206 c between point 205 and the apex of cornea segment C is 13.5 mm. Cornea radius 207 (radius r) is 7.8 mm. If the eye is illuminated with a collimated beam of infrared light, the cornea will reflect approximately 4% of the light. The reflected light has a virtual focus on the corneal focal plane. This virtual focus forms the First Purkinje FP image (First Purkinje point) 301 in FIG. 3A. In FIG. 3A is shown a sketch 300 of formation of FP image 301 where the distance d 302 between the center of eye rotation CR 205 and the cornea focal plane is typically 9.6 mm. FIG. 3B shows schematic 3000 that illustrates the key principles of how the eye rotates and its effect on cornea focal plane 3002. When eye 3001 rotates an angle α 3003, (aiming in the required gaze direction), the center of cornea focal plane 3002 moves from the point F to the point F', where segment FF'=2*9.6*sin(α/2) mm. First Purkinje point FP 3004 moves less far in the direction FF', and thus moves relative to the eye in the opposite direction on segment F'FP which is equal to (r/2)*sin(α) or (3.9)*sin(α) mm. Therefore, the position of the first Purkinje image is shifted a distance on line segment 3005 of Δ where:

$$\Delta = 2*9.6*\sin(\alpha/2) - (3.9)*\tan(\alpha) \quad (1)$$

When both eyes are targeted on an object located at a distance D, each eye rotates inwards through a parallax angle α=(E/2)/D, where E is the eye separation distance. The approximation for small α is adequate for the present purpose. For a statistically average person E=60 mm. Therefore, when both eyes are rotated so as to be fixed on an object located at the distance D from the observer, the change in the distance R (which is the distance between the first Purkinje points of the left and right eye in FIG. 1) can be calculated using Eq. 2:

$$\Delta R = 2[2*9.6*\sin(30/2D) - (3.9)*\tan(30/D)] \quad (2)$$

where D is the distance to the object in mm. To a sufficient degree of approximation, ΔR can be treated as independent of the direction of the user's gaze.

The present eye tracker can be integrated into eyewear that determines the eyes' focusing distance D via the position of the aforementioned first Purkinje points. By knowing the change ΔR of the distance R 107 between First Purkinje points FP, the focusing distance D can be calculated from Eq. (2) and the system controller can generate the required driving signal for the focusing hardware.

Figure 5:
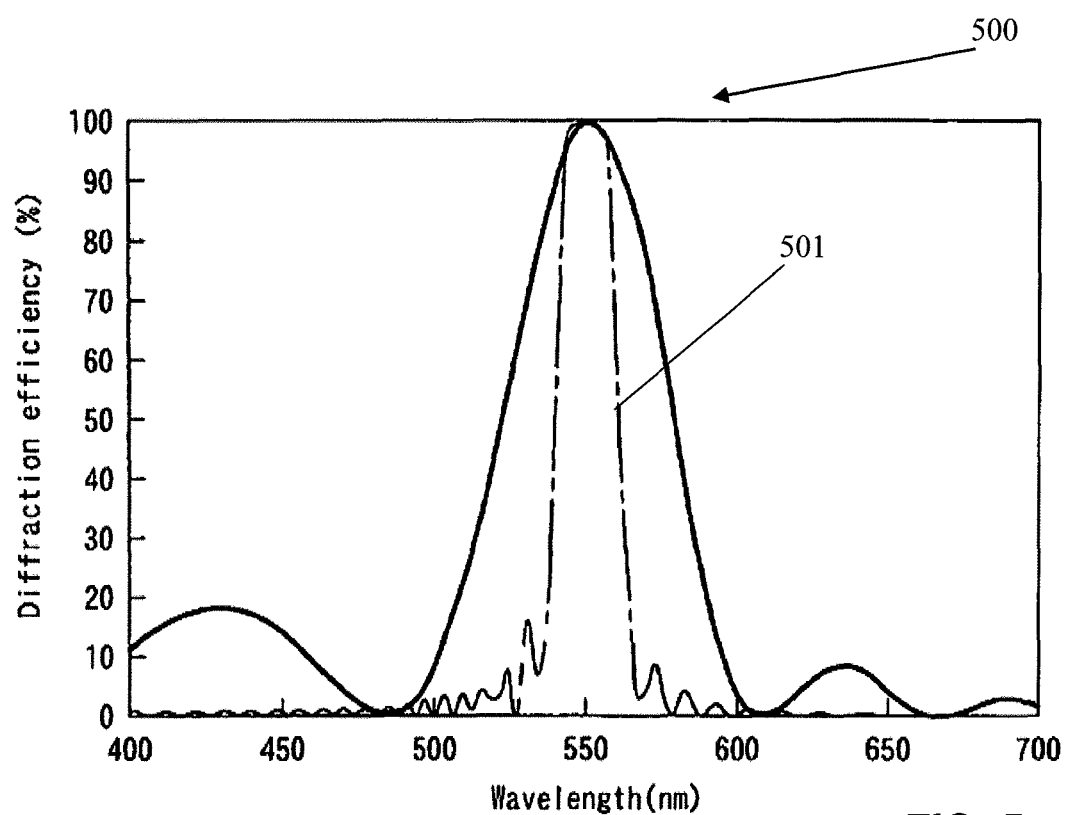
FIG. 5 is a graph of the efficiency of reflection and transmission volume holograms as a function of the difference between the recording and read-out wavelengths.

A schematic of an embodiment of parallax tracker 400 of the present invention is shown in FIG. 4. It consists of two subsystems integrated into a pair of eyewear lenses. Illumination subsystem 401 provides near-infrared light that illuminates both corneas with a collimated near-infrared beam. Purkinje point imager subsystem 402 provides an image of the First Purkinje point 403 (one for each eye). Illumination subsystem 401 has an aspherical single lens collimator 404 that collimates the light output from a near-infrared laser diode 405 and injects the collimated light into each eye glasses lens 101 through a beamsplitter 406. The light propagates inside the lens by total internal reflection. A volume reflection hologram (VRH) 407 is laminated or imbedded into the lenses in the front of each eye and is designed to be selective for specific wavelengths. FIG. 5 shows graph 500 calculated in Ref. [3] for the recording wavelength 550 nm which gives the diffractive efficiency of both reflection and transmission holograms as a function of an operational wavelength that is different from the recording wavelength. FIG. 5 shows that volume reflection hologram has an efficiency shown in the graph 501 and interacts with incoming light within a very narrow band of ±15 nm around the recording wavelength. In the present embodiment, the tracker hologram is recorded and operates at a wavelength of 780 nm, and so does not interact with the incoming visible light from the scene, which is in the waveband from 400 nm to 700 nm (starting 80 nm below the recording wavelength).

The near-infrared beam interacts with VRH 407 and is redirected to each eye. The cornea reflection from this collimated beam has a virtual focus at First Purkinje point 403 for each eye. The reflected light from the cornea is redirected back to the eye wear lens. This reflected light is redirected by the VRH through each eye glasses lens back to the edge of the lens by total internal reflection. Upon leaving the spectacle lens at its lateral edge side, the reflected light is focused by a tracker lens 408 onto a compact CCD (or PSD) receiver 409. As explained above, the positions of the First Purkinje points change when the eyes focus at different distances. The tracker controller calculates the position of the Purkinje point for each eye. The positions of the two Purkinje points are compared and the parallax shift ΔR is calculated. From the parallax shift ΔR, Eq. (2) yields the distance D 109 to the object of interest, and thence the refocusing distance ΔD. A drive signal for the focusing system is generated once the refocusing distance ΔD is known.

An embodiment of the optical system of tracker imager 600 is shown in FIG. 6 with representative rays illustrative of its operation. When an eye is rotated, the first Purkinje points are located on the spherical surface 601 which has a typical radius of 9.6 mm. The divergent reflected beam from any Purkinje point (located on surface 601) is sent into eye wear lens 602 and reaches the VRH 603. The VRH is recorded so as to operate with two wavefronts. The first one is incoming from the eye side and is represented by flat wavefront 701 shown in FIG. 7. The second wavefront 702 is reflected inside waveguide and is represented by principal ray 703. The reflected beam propagates in the guide via total internal reflection angle.

Figure 7:
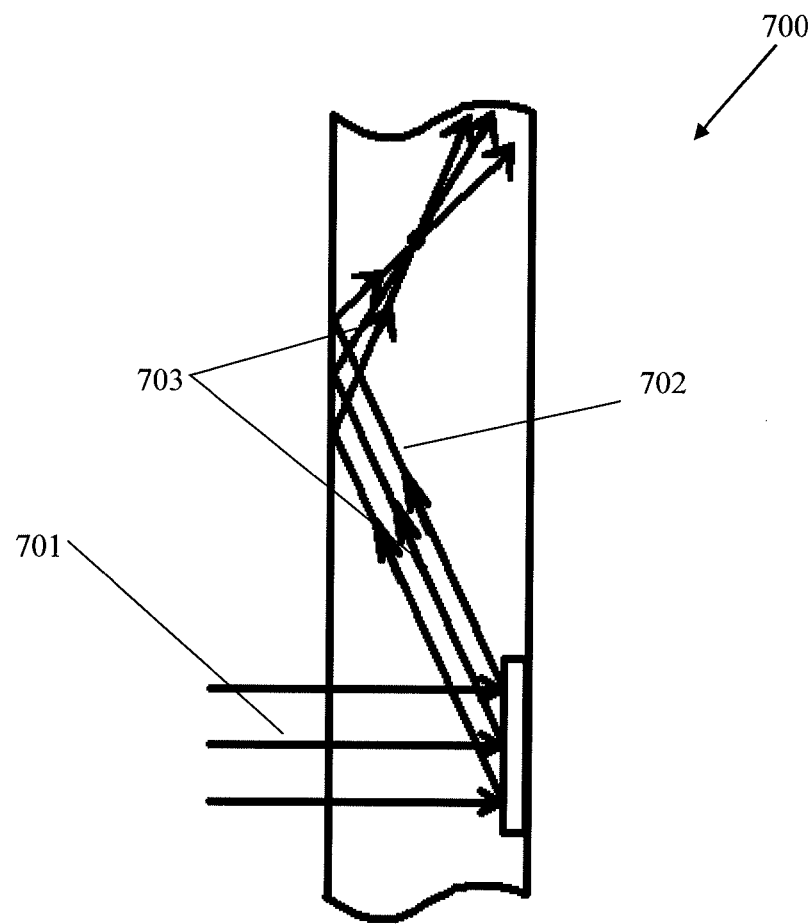
FIG. 7 is a sketch of an operational scheme of a reflection volume hologram.
Figure 8:
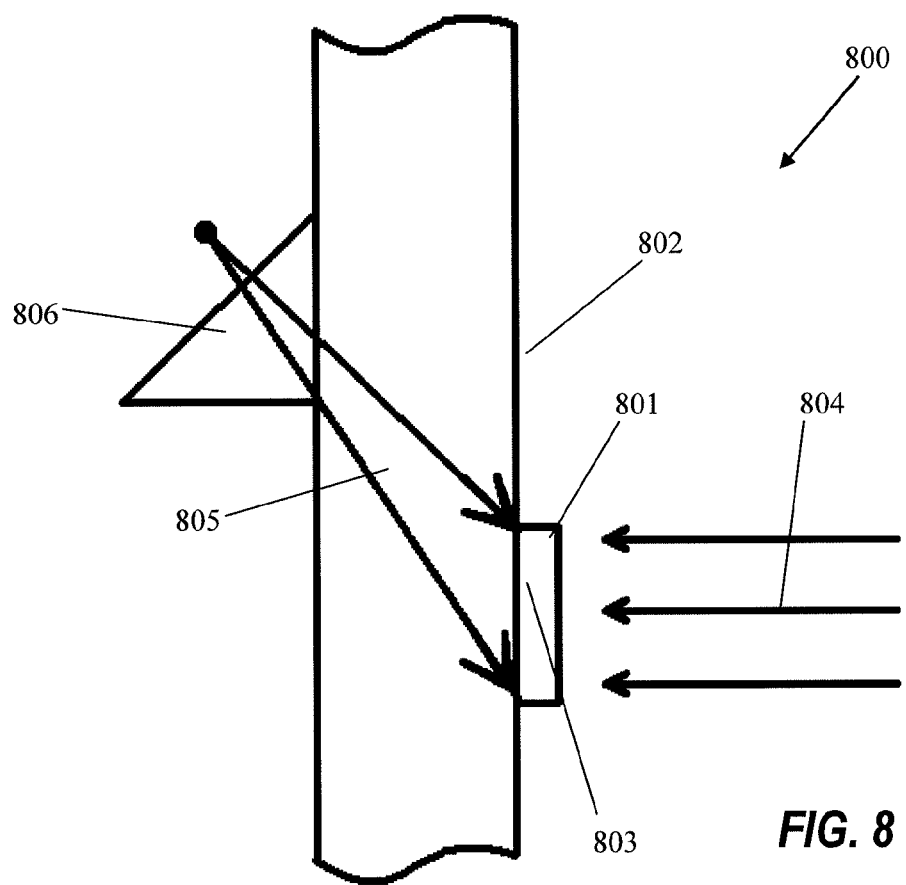
FIG. 8 is a sketch of a volume-hologram recording setup.
Figure 9:
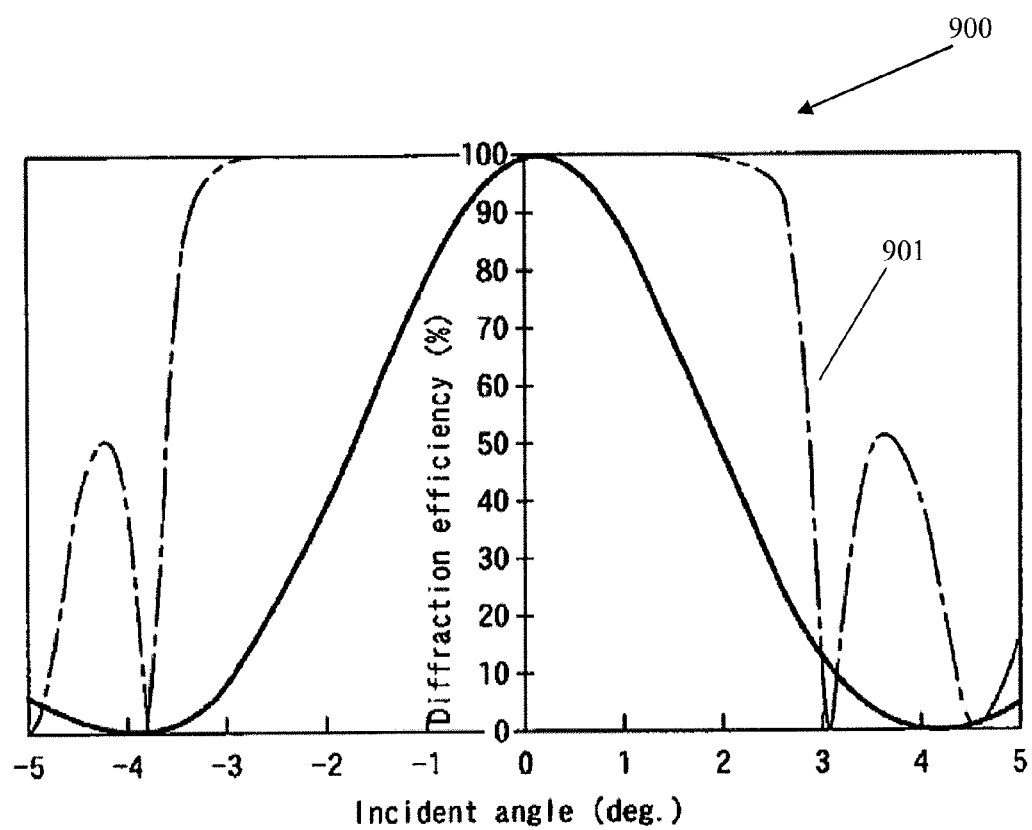
FIG. 9 is a graph of the efficiency of reflection and transmission volume holograms as a function of the difference of the incidence angles between the recording and read-out beams.

An embodiment of a recording scheme 800 for this volume hologram is shown in FIG. 8. In FIG. 8, hologram substrate 801 is attached to waveguide 802. Recording holographic medium 803 is located at the interface between these plates. There are some technical difficulties in making a convergent beam corresponding to beam 702 in the recording scheme. So the hologram is recorded with two beams coming in opposite directions to beams 701 and 702 as illustrated in FIG. 8. These beams are 804 and 805 in FIG. 8. Thus, a diverging beam 805, which is easier to generate, can be used instead of a converging beam. As a consequence of the duality principle of VRH, explained in Ref. [4], the hologram reflects incoming beam 701 in the direction of beam 702 as shown in FIG. 7. Divergent beam 805 is injected into waveguide through a prism 806 with an incidence angle insuring total internal reflection of said beam within the waveguide. The volume reflection hologram efficiency is very sensitive to the difference in the incidence angles of incoming rays vs. the incidence angle of recording rays. FIG. 9 shows VRH efficiency graph 900 as a function of the incidence angle represented by chain-dashed line 901, see Ref [3]. It is apparent from FIG. 9 that such a reflection hologram operates in a narrow ±5° angular band, where the angle is determined by the difference in angle between the recorded and operating rays. Therefore, only those beams reflected from any Purkinje point with a principal ray orthogonal to the hologram and having a divergence of ±5° around it, will be reflected by the hologram.

Tracker imaging scheme 600 (FIG. 6) is designed to be telecentric in object space with a 5 degrees object aperture. After a reflection at hologram 603, the beams are focused at plane 604 and propagate inside the lens via total internal reflection conditions. One embodiment uses an eye wear lens made from polycarbonate. For this material the angle of propagation through the lens is approximately 45°. From any location for the First Purkinje point, in the configuration shown in FIG. 6 there are four TIR reflections of the beams before reaching exit surface 605. Upon exiting at 605 the beam is focused on sensor (CCD or PSD) 606 through the use of split triplet 607. The components of the triplet are optimally decentered to compensate for the field coma of the hologram. Triplet 607 has two biconical surfaces. First biconical surface 608 is designed to compensate for the variable quadratic astigmatism over the field. Second biconical surface 609 compensates the constant for field astigmatism related to the volume hologram. The radiuses and thicknesses for the optical prescription for this embodiment of this imaging scheme are shown in Table 1. All components are of zero conicity (eccentricity).

The decentering values related to the components are shown in Table 2.

TABLE 2

| Surf. # | Surface Type | Decentering Y (mm) | Tilt about X (degr.) |
|---|---|---|---|
|  | Object |  |  |
| 1 | Standard |  |  |
| Stop | *Hologram 2 |  |  |
| 3 | Standard |  |  |
| 4 | Standard |  |  |
| 5 | Standard |  |  |
| 6 | Standard |  |  |
| 7 | Coord. Break | 39. | 45. |
| 8 | Standard |  |  |
| 9 | Coord. Break | 0.62 | 0.75 |
| 10 | Standard |  |  |
| 11 | Standard |  |  |
| 12 | Coord. Break | 0.52 | −1.04 |
| 13 | Biconic |  |  |
| 14 | Standard |  |  |
| 15 | Coord. Break | −0.15 | −0.70 |
| 16 | Standard |  |  |
| 17 | Standard |  |  |
| 18 | Coord. Break | 0.072 | −1.40 |
| 19 | Standard |  |  |
| 20 | Biconic |  |  |
| 21 | Coord. Break | 0.71 | −5.44 |
|  | Image |  |  |

The imager operates with an input field of ±2.3 mm and an output field of ±1.55 mm. A compatible size CCD camera for the aforementioned tracker imaging system is ¼ inch, which has an active long length of 3.2 mm. As the tracker imager input field height being measured in the eye is 2.3 mm and the distance from a First Purkinje point to the center of eye rotation is 9.6 mm, then the system can handle a rotation of the eye of ±15°. Further, in convergence the eye actually rotates only in one direction (not outward but inward only). So for objects located directly in front of the user's head the

TABLE 1

| Surface # | Surface Type | Radius mm | Thickness mm | Glass | Semi Diam. mm | X radius mm |
|---|---|---|---|---|---|---|
|  | Object | −9.6 | 20. |  | 2.3 |  |
| 1 | Standard | Infinity | 7. | Polycarb |  |  |
| Stop | *Hologram 2 | Infinity | −7. | Mirror | 3.3 |  |
| 3 | Standard | Infinity | 8. | Mirror |  |  |
| 4 | Standard | Infinity | −8. | Mirror |  |  |
| 5 | Standard | Infinity | 8. | Mirror |  |  |
| 6 | Standard | Infinity | −8. | Mirror |  |  |
| 7 | Coord. Break | Infinity |  |  |  |  |
| 8 | Standard | 17.789 | −5. |  | 3. |  |
| 9 | Coord. Break |  |  |  |  |  |
| 10 | Standard | −9.8317 | −1. | Polycarb | 3.1 |  |
| 11 | Standard | −20. | 0. |  |  |  |
| 12 | Coord. Break |  | −1. |  |  |  |
| 13 | Biconic | −6.7769 | −1.5 | Polycarb |  | 10.832 |
| 14 | Standard | 28.3253 | 0. |  |  |  |
| 15 | Coord. Break |  | −1. |  |  |  |
| 16 | Standard | 61.4354 | −1.5 | Polycarb |  |  |
| 17 | Standard | 16.5232 | 0. |  |  |  |
| 18 | Coord. Break |  | −0.5 |  |  |  |
| 19 | Standard | 7.3183 | −1.5 | Polycarb |  |  |
| 20 | Biconic | −2.512 | 0. |  |  | 5.1964 |
| 21 | Coord. Break |  | −7.845 |  |  |  |
|  | Image | Infinity |  |  | 1.6 |  |

*Hologram 2 has the following construction coordinate points (in the hologram coordinates system):

Construction point 1: z1 = infinity

Construction point 2: y2 = 25 mm; z2 = −25 mm; wavelength in the optical material 0.495 micrometers; diffraction order 1.

tracker can track the full eye movement of 15 degrees of convergence of each eye. This 15 degrees convergence of both eyes means that the eye is retargeting from infinity (no convergence of eyes) down to 100 mm target distance (full convergence). The symmetrical field was chosen so the system can focus on objects that are located within the azimuthal position of ±15°, at any distance out to infinity.

Figure 10:
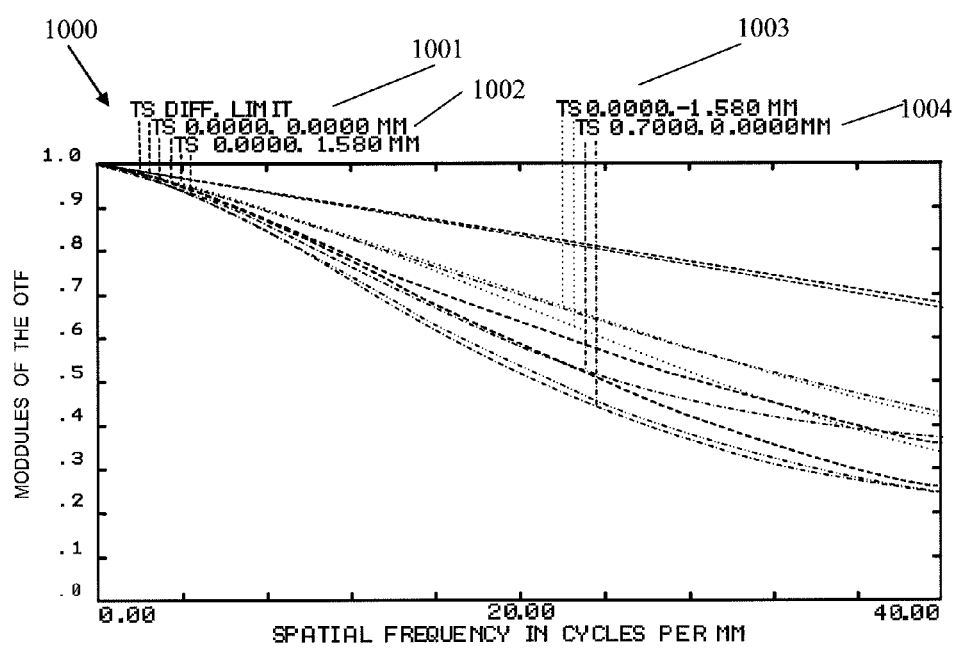
FIG. 10 is a graph of modulation transfer functions for a preferred embodiment for the gaze tracker subsystem.

FIG. 10 shows optical transfer functions 1000 of the imager for different field of view points, 1001, 1002, 1003 and 1004. For each point, the x and y coordinates in the image plane are given in mm, with 0, 0 being the center of the image area. Curves are given for the optical transfer function (OTF) in the tangential (T) and sagittal (S) directions for each point. A pair of curves for the diffraction limited OTF are provided for comparison. The conventional criterion for resolution states that the minimum contrast resolution has to exceed 0.3. Therefore, this embodiment of the imager can resolve 38 pl/mm at the image plane. This means that the tracker will have 240 resolved positions imaged onto the 3.2 mm sized receiver. The 240 tracker resolved positions results in an angular resolution of 0.12°, starting from the parallax angle (0°) all the way up to 15° in the maximum convergent position. For the 1 m distance it means 0.07 m of focusing accuracy. The accuracy of focusing distance for the closer distances improves, reaching 4 mm at the distance of 250 mm.

Figure 11:
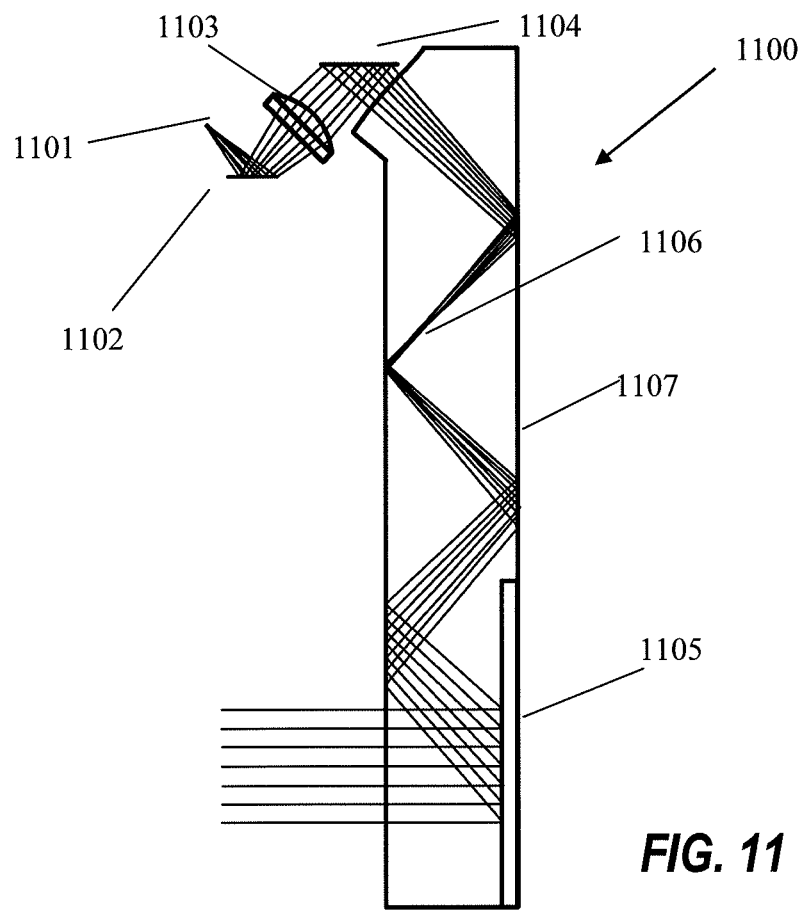
FIG. 11 is an optical layout of a preferred embodiment of an illumination subsystem of an integrated gaze tracker.

The layout of an embodiment of tracker illumination system 1100 is shown in FIG. 11. The source has wavelength of 780 nm wavelength from a fiber coupled laser diode. The fiber core diameter is 15 microns. The fiber end is shown at position 1101. The fiber output is reflected by mirror 1102 and is refocused to point 1106 using single aspherical lens 1103. Beamsplitter mirror 1104 redirects the beam to eyewear guide 1107. This beamsplitter mirror corresponds to mirror 406 shown in FIG. 4. The illumination and imaging optical tracks of the tracker are combined through this beamsplitter. The beam propagates by total internal reflection. Upon reaching volume reflection hologram 1105, the collimated beam is reflected to the eye.

An optical prescription for the illumination system is shown in Table 3 and the aspherical coefficients with decentering parameters are shown in Table 4. All components are of zero conicity (eccentricity).

TABLE 3

| Surf. # | Surface Type | Radius mm | Thickness mm | Glass | Semi Diam. mm |
|---|---|---|---|---|---|
| | Object | Infinity | Infinity | | |
| 1 | Standard | Infinity | 10. | | |
| 2 | Standard | Infinity | 7. | Polycarb | |
| Stop | *Hologram 2 | Infinity | −7. | Mirror | 3.3 |
| 3 | Standard | Infinity | 8. | Mirror | |
| 4 | Standard | Infinity | −8. | Mirror | |
| 5 | Standard | Infinity | 8. | Mirror | |
| 6 | Standard | Infinity | −8. | Mirror | |
| 7 | Coord. Break | Infinity | | | |
| 8 | Standard | 17.789 | −2.2 | | 3. |
| 9 | Coord. Break | | 0. | | |
| 10 | Standard | Infinity | 0.. | Mirror | |
| 11 | Coord. Break | | 4. | | |
| 12 | **Even Asphere | 3.7698 | 1.5 | Polycarb | |
| 13 | Standard | Infinity | 3.5 | | |
| 14 | Coord. Break | | 0. | | |
| 15 | Standard | 1475. | 0. | Mirror | |

TABLE 3-continued

| Surf. # | Surface Type | Radius mm | Thickness mm | Glass | Semi Diam. mm |
|---|---|---|---|---|---|
| 16 | Coord. Break | | −4.1379 | Polycarb | |
| 17 | Coord. Break | | 0. | | |
| | Image | Infinity | | | |

*Hologram 2 has the following construction coordinate points (in the hologram coordinates system): Construction point 1: z1 = infinity Construction point 2: y2 = 25 mm; z2 = −25 mm; wavelength in the optical material 0.495 micrometers; diffr. order 1.
**The Even Aspherical surface 12 has 4-th order coefficient −1.38604E−3 and 6-th order coefficient −1.6118E−4

TABLE 4

| Surf. # | Surface Type | Decenterings Y (mm) | Tilt about X (Degrees) |
|---|---|---|---|
| | Object | | |
| 1 | Standard | | |
| 2 | Standard | | |
| Stop | *Hologram 2 | | |
| 3 | Standard | | |
| 4 | Standard | | |
| 5 | Standard | | |
| 6 | Standard | | |
| 7 | Coord. Break | 39. | 45. |
| 8 | Standard | | |
| 9 | Coord. Break | | 45. |
| 10 | Standard | | |
| 11 | Coord. Break | | 45. |
| 12 | *Even Asphere | | |
| 13 | Standard | | |
| 14 | Coord. Break | | −45 |
| 15 | Standard | | |
| 16 | Coord. Break | | −45. |
| 17 | Coord. Break | −0.025 | |
| | Image | | |

The illumination scheme of FIG. 11 and Tables 3 and 4 can deliver a high quality collimated beam that has close to zero aberrations to the eye. The beam divergence is 0.04°. Such a divergence means that the First Purkinje point for an average person's cornea, which has a focus of 3.9 mm, will have a diameter on the eye of 2 microns. The imaging system has magnification of 0.69. Therefore, the blurring, which is due to the illuminated beam divergence, will be insignificant and will result in only an additional 1.3 microns at the sensor plane.

In Eq. (2) the change in distance −ΔR between First Purkinje points was calculated using the parameters of the average adult eye. The general equation for the distance ΔR is:

$$\Delta R = 2[2*Q*\sin(E/4D) - (r/2)*\tan(E/2D)] \quad (3)$$

where:
Q is the distance between the center of eye rotation (point CR in FIG. 3) and the cornea focal plane, which for the average eye is equal to 9.6 mm;
E is the distance between eye centers, (60 mm for the average eye); and
r is the cornea radius (for average eye 7.8 mm).

These parameters will likely be slightly different for each individual. Parameters Q and r are correlated. Typically, $Q = 1.23\,r$, whereas the parameters E and r are independent of each other. Therefore, the above equation can be simplified as:

$$\Delta R = r[4.92*\sin(E/4D) - \tan(E/2D)] \quad (4)$$

Ideally the gaze tracking system should be calibrated for each user. A simple way of calibrating is to set both variable focus lenses to zero power and then ask the user to look at an object located at a far distance (infinity or near to infinity) and to look a second time at the typical reading distance of 250 mm. For each user, the tracker controller can measure the eye separation E as the distance R between cornea reflections when the gaze directions are parallel (object at infinity); measure R when the gaze directions converge to the reading distance D=250 mm; calculate ΔR from the two measured values of R; and calculate r from Equation 4. The values of r and E for the individual user are then stored in non-volatile memory in the controller 102. After calibration the gaze tracker will use the individual parameters r and E for accurate and efficient driving of the custom autofocusing glasses. Comfortable vision distance 111 has to be determined at the optometrist office and be programmed into controller 104. After these two calibrations are made the autofocusing eyewear is ready to deliver to the presbyopia patient for continuous everyday comfortable vision.

Figure 12:
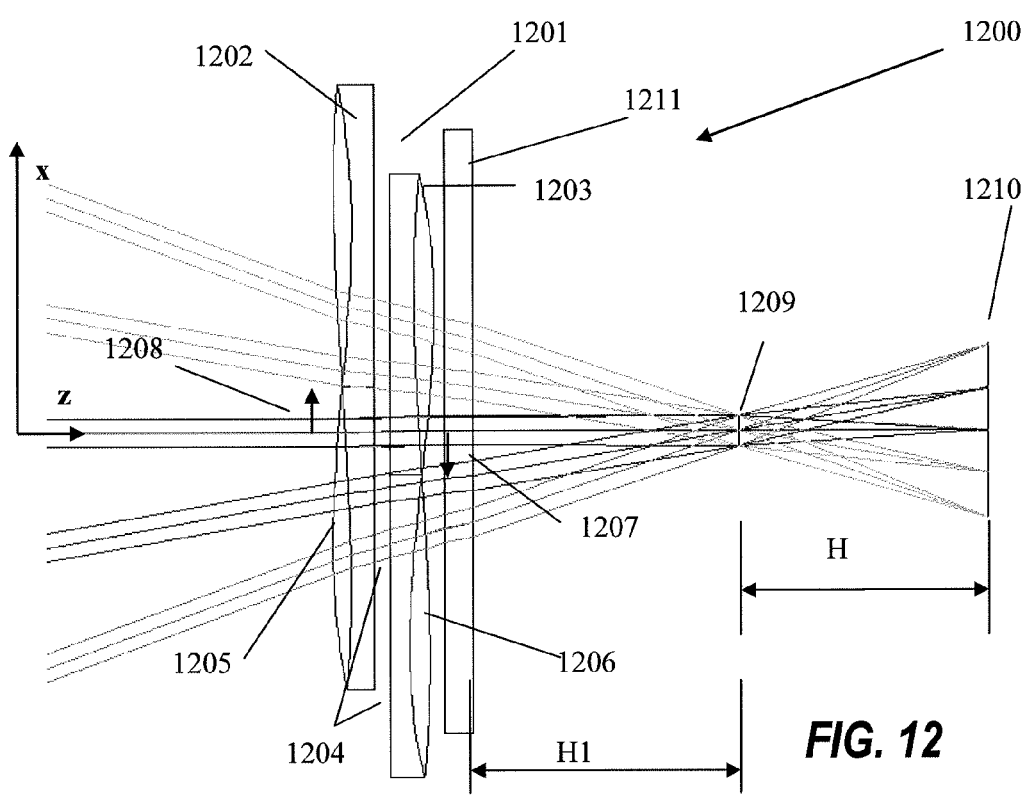
FIG. 12 is a schematic diagram of a preferred embodiment of an eyewear variable optical power component.

FIG. 12 shows the optical layout of a preferred embodiment of an autofocusing optical assembly 1200 of the autofocusing eyewear. Autofocusing optical assembly 1200 consists of variable power optical component (VPOC) 1201 and plano-parallel eye-tracker waveguide 1211, both made from optical-grade polycarbonate. VPOC 1201 is an optimized Alvarez lens [5]. The lens consists of two components 1202 and 1203. Each component has an internal flat surface 1204 and an aspherical outer surface, respectively 1205 and 1206. The central thickness of both components is 2.2 mm. The central thickness (corresponding to Alvarez's constant term E) has very little optical effect, and may be chosen as a compromise between weight and strength. The sag z of the aspherical surfaces is:

$$z = A(x*y^2)/s^3 + B(x^3)/s^3 + D(x)/s \quad (5)$$

where the x-axis and z-axis are located in the plane of FIG. 12 and the y-axis is orthogonal to the plane of the drawing, and where s=25, for surfaces 1205 and 1206. In an example of a lens for a patient with 3 diopter myopic presbyopic eyes, for the surface 1205: A=6, B=1.890742 and D=−1.6. For surface 1206: A=−6.962333, B=−2.201143 and D=1.6. A, B, D, and s are in millimeters. The Dx term is an inclination of the surface, and can be used to make the thickness of the plate more uniform. D may be chosen to minimize ($z_{max} - z_{min}$) for either component, or for an average of the two. If D for one surface is not equal to −D for the other surface, the overall thickness of the Alvarez lens will vary as it is adjusted, and may show a prismatic component. That may be useful for some purposes, but usually it is preferred for the two D terms to be equal and opposite.

The prior art Alvarez lens of Ref. [5] has symmetrical front and back components with coefficients B=(⅓) A. The presently proposed "upgraded Alvarez lens" utilizes an asymmetrical design for the front and back components and the values of the A and B coefficients differ from the prior art 1 to 3 proportion. These are the main two differences between the classical and upgraded versions of the Alvarez lens. Further, when front component 1202 is moved in the x direction on segment 1208 (u) and the back component is moved in the opposite direction on segment 1207 (−u), the lens changes its optical power.

The 2 mm waveguide plate is located at the 1.5 mm axial distance from the VPOC.

In the following example the eye is simulated with an unaberrated paraxial lens 1209 having a fixed focal length of 16.2 mm. The optical performance simulation was made at the wavelength 0.55 microns. The pupil diameter is assumed to be 2 mm. Segment H between eye lens and retina plane 1210 is 17 mm. Hence the eye is 3 Diopters nearsighted and because it does not change the focal length during refocusing process it is completely presbyopic. The axial distance H1 between the waveguide and the eye lens is 18 mm. The whole optical system has a 40° field of view in the plane of FIG. 12 (horizon plane) and a 30° field of view in the vertical plane. To focus the system at different distances the front and back components 1202 and 1201 are moved in the opposite directions on segments u shown in Table 5.

TABLE 5

| | Distance to the object (mm) | | | |
|---|---|---|---|---|
| | 20000 | 1000 | 310 | 250 |
| Travel u (mm) | 2.927 | 2.02 | 0. | −0.55 |

Figure 13:
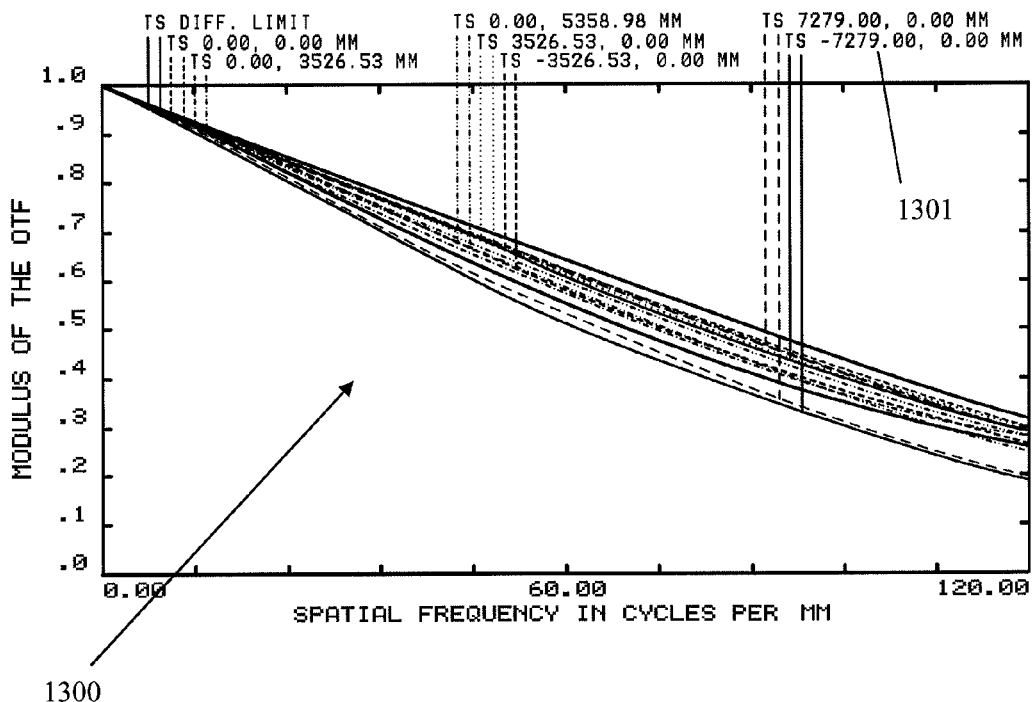
FIG. 13 is a graph of modulation transfer functions for a preferred embodiment of a variable power lens applied for vision correction of a nearsighted presbyopic eye for vision at 20 meters distance.
Figure 14:
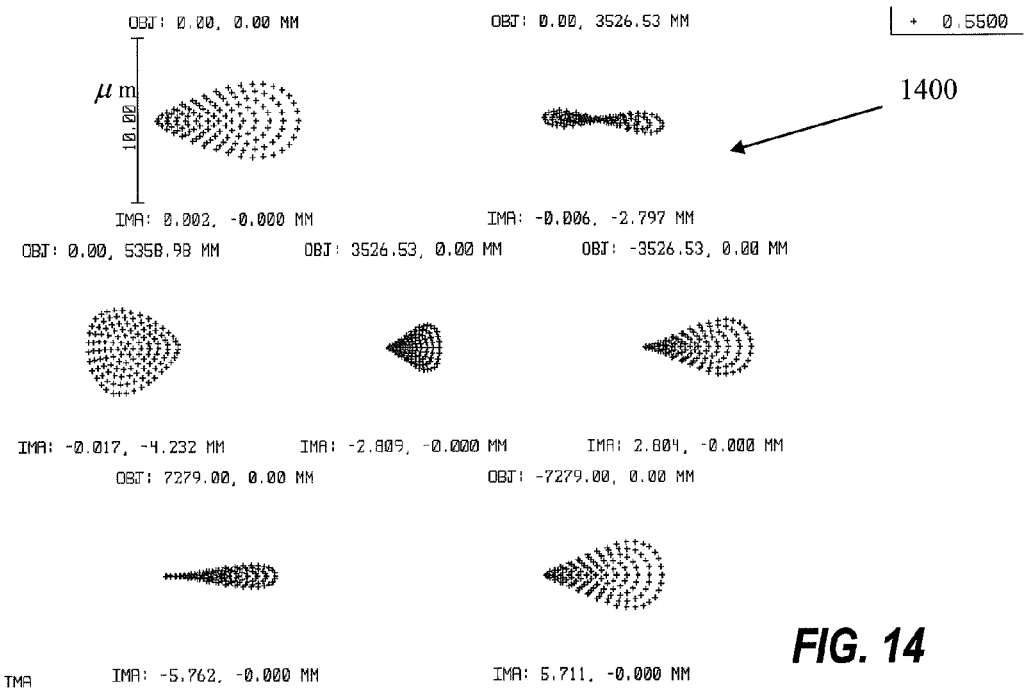
FIG. 14 is a graph of point spread functions for a preferred embodiment of the variable power lens applied for the vision correction of the nearsighted presbyopic eye for the vision at 20 meters distance.
Figure 15:
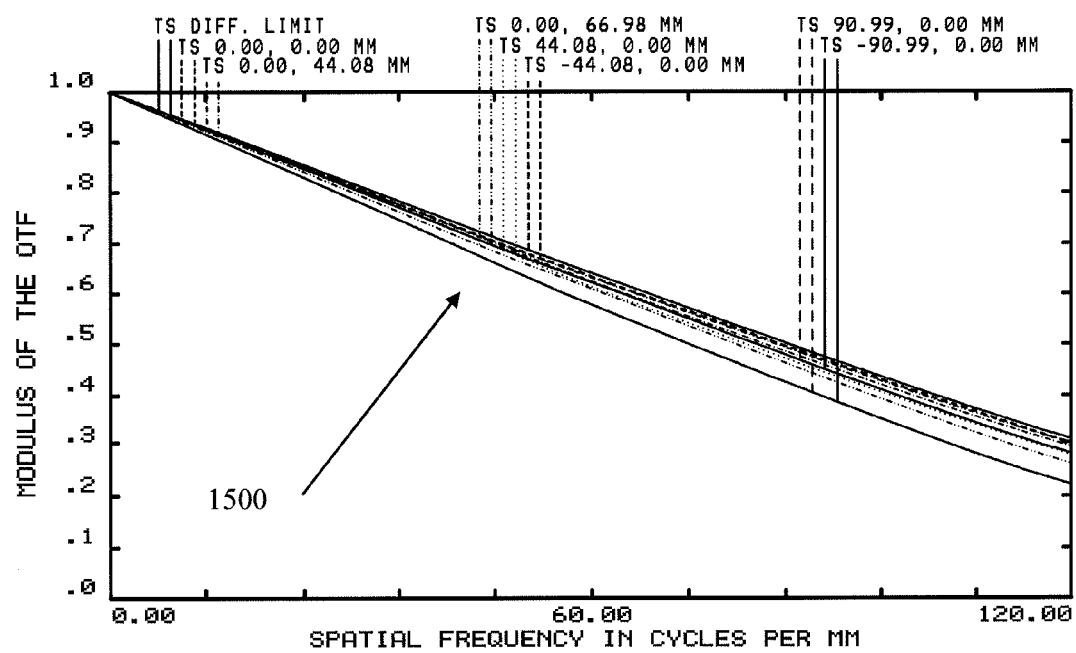
FIG. 15 is a graph of modulation transfer functions for a preferred embodiment of the variable power lens applied for the vision correction of the nearsighted presbyopic eye for vision at 250 mm distance.

The modified Alvarez lens (with a wider field of view than the one revealed in U.S. Pat. No. 3,305,294) in combination with the eye, creates a diffraction limited quality image at retina 1210. FIG. 13 shows modulation transfer functions 1300 for the system, when there is focus distance of D=20,000 mm. Coordinates of the field points 1301 are shown in mm in the x-y plane at z=D. For example, coordinates x=−7279 mm and y=0 mm means that this point, which is located at a distance of 20 meters, is viewed by eye horizontally in the direction of −20° in the x direction. The field points in the FIG. 13 will be viewed by the eye straight ahead, and in the directions of ±10° and ±20° in the horizontal plane and +10° and +15° in the vertical (y) plane. The point spread functions 1400 for the position of the object at a distance of 20 meters are shown in FIG. 14. All spots at the retina are less than 10 microns in size. The modulation transfer functions 1500 when the system is focused at the distance 250 mm is shown in FIG. 15. So the modified Alvarez lens shown in FIG. 12 has a refocusing power of 4 Diopters and can provide refocusing from infinity distance to the reading distance of 250 mm for the nearsighted presbyopic eye. The nearsighted patient can focus their eye at the any distance located between infinity and 250 mm. In addition, some correction for myopia can be included in the modified Alvarez lens.

For such moderately nearsighted presbyopic patients, the "neutral" position of the front and back components 1202 and 1203 (at which u=0, and the x=0 points of both lenses coincide at the forward axis of the eye) is at the comfortable vision distance, and the direction of travel changes sign at the comfortable vision distance (see Table 5).

For patients having presbyopia and farsightedness there is no such self focusing distance in the range between infinity and 250 mm. Even focusing at infinity will require some initial value u for travel distances 1208 and 1207, and for refocusing at a closer distance the value of the components' travel distance will increase. The value of the travel parameter u for focusing at the reading distance may therefore be unacceptable from a mechanical point of view. For farsighted patients a conventional vision correction lens can be mounted in front of the Alvarez lens. The correction lens may be chosen to correct the eye to an emmetropic state, or to overcorrect for farsightedness, creating in effect the moderately near-sighted patient that the Alvarez lens can most effectively accommodate.

For severely nearsighted presbyopic patients, for whom the natural comfortable vision distance is closer than the desired reading distance, a conventional vision correction lens with the opposite correction may be needed.

For moderately nearsighted patients, the optics of the autofocusing eyewear will be a sandwich of the VPOC shown in FIG. 12 or another available variable power component, see, for example, Ref. [6], and the thin waveguide plate of the parallax tracking system shown in FIGS. 6, 11. For farsighted patients, the optical sandwich may have a conventional prescription lens at the front of sandwich or may operate without such a prescription lens depending on the type of the variable power component. To support 20/20 vision acuity, standard presbyopic patients having different focal length of eye lens has to use different prescription of the modified Alvarez lens. For example the Alvarez lens for patients with inflexible intraocular lens implant, forming an emmetropic eye having 17 mm focal length, will have for the surface 1205 coefficients A=6, B=1.860846, D=−1.6 and for surface 1206 coefficients A=−7.034551, B=−2.188646 and D=1.6.

More generally, $A_{1205}$ may be in the range from 5 to 8, but the optimum value is typically close to 6. $A_{1206}$ may be in the range from −6.5 to −8.5, and is related to the maximum value of u. For example, lenses with 4 diopters power range may have $A_{1206}=-7.034$, $u_{max}=3.66$ mm, or $A_{1206}=-8.212$, $u_{max}=3.1$ mm. The lower maximum value of travel u is mechanically attractive, but by $A_{1206}=-8.212$ the image quality starts to deteriorate.

The preceding description of the presently contemplated best mode of practicing the invention is not to be taken in the limiting sense, but is made merely for the purpose of describing the general principles of the invention.

Various modifications may be made. For example, if the patient's two eyes have slightly different myopia $D_0$, that may be corrected for by slightly offsetting the value of u between the two eyes. However, that reduces the range of adjustment of the overall eyewear, because at each extreme one lens will reach the end of its travel before the other. Except for very small differences in the myopia correction between the two eyes, therefore, it is preferred to provide a conventional correction lens in front of the modified Alvarez lens. It is estimated that a difference of up to 0.3 or 0.4 diopters obtained by offsetting the u=0 points could be acceptable. In the U.S.A., where eyeglass prescriptions are typically measured in steps of 0.25 diopters, that would in practice allow a correction of one 0.25 diopter step in the prescription.

As explained above, some optical correction can be included in the design of the modified Alvarez lens, analogously to the terms $Bx^2+Cxy+F(y)$ in Alvarez's original equation, which are not used in the present embodiment. (The coefficient B is different in the present application and in Alvarez's original equation. Coefficient B in Equation 5 above corresponds to coefficient ⅓ A in Alvarez's original term ⅓ $Ax^3$.) However, such corrections increase the complexity of the modified Alvarez lens, and may cause distortion that varies as the lens components are displaced. A separate correcting lens that does not move as the modified Alvarez lens is adjusted may therefore be provided instead of, or in addition to, including an optical correction in the modified Alvarez lens.

The novel modified Alvarez lens differs from Alvarez's original design in that where Alvarez originally specified identical coefficients for the two lenses, a fixed ratio B=⅓ A, and a value of A=6, the present modified Alvarez lenses have different coefficients for the two lenses, and/or B≠⅓ A for at least one lens, and/or A≠6 for at least one lens.

The eyewear may be colloquially referred to as "glasses" or "eyeglasses" but, as described above, that does not imply that the optical material of the eyewear, or of any particular component thereof, is glass. Any suitable optical material may be used, and the skilled reader will understand how to select a suitable optical material or materials having regard to relevant properties including hardness, weight, and refractive index.

In the embodiment, the eyewear comprises, in order away from the eye, a waveguide for the illumination and imaging systems; a variable-power lens in the form of a modified Alvarez lens; and optionally a fixed-power spectacle lens. Other arrangements are possible. For example, a gaze-tracker that does not also correct for presbyopia might omit the variable power lens. For example, the fixed power lens and the waveguide may be combined into a single element, especially in a unit with no variable-power element.

In the embodiment, the parallax tracker will track movement of each eye up to 15° either side of straight ahead. It will be appreciated that, especially when the user's gaze both converges on a nearby object and is directed sideways, one or both eyeballs may turn more than 15° from straight ahead, and tracking of one or both first Purkinje points may be lost. If necessary, the tracking range can be increased, especially on the side of each eye towards the nose. Alternatively, or in addition, the autofocusing system can be programmed to respond to loss of tracking. In most cases the preferred approach is to retain the last focus setting determined before tracking was lost. It is believed that most users can readily be trained to reestablish tracking, either by turning the head towards the gaze direction or by turning the gaze towards the straight ahead direction. However, in appropriate cases, other approaches, such as resetting the variable power eyewear to infinity or another preselected focus distance, may be programmed.

In the embodiment, the eyewear is essentially a pair of spectacles for a human being. However, any arrangement may be used that maintains the illumination and scanning waveguide in a sufficiently steady position in front of two eyes that converge to view an object of interest, and that have projecting corneas to form First Purkinje points spaced from the centers of rotation of the eyes.

The full scope of the invention should be determined with reference to the Claims.

REFERENCES

1. T. Duchovski, "Eye tracking methodology" Springer, 2007.
2. T. Cornsweet, H. Crane, "Accurate two-dimensional eye tracker using first and fourth Purkinje images", JOSA, Vol. 63, No. 8, pp. 921-928, 1973.
3. U.S. Pat. No. 7,418,170 by Mukawa et al.
4. R. Collier, C. B. Burckhardt, L. H. Lin, *Optical Holography*, Academic Press, 1971
5. U.S. Pat. No. 3,305,294 to L. W. Alvarez
6. www.superfocus.com

What is claimed is:

1. An eye parallax tracking system, comprising: a pair of eyewear with waveguides in each eyewear lens, said waveguides being transparent so as to permit a wearer to view an external scene directly; an illumination subsystem arranged to direct a beam of collimated light onto a wearer's eyes through said waveguides; a First Purkinje point imaging subsystem for each said lens using light from said illumination system reflected from said eyes through said waveguides; and a controller operative to calculate from the positions of the First Purkinje points of the wearer's eyes a quantity representative of at least one of the wearer's gaze parallax angle and the distance to an object of interest on which the gaze of the wearer's eyes converges.

2. The eye parallax tracking system of claim 1 wherein each said illumination and First Purkinje points imaging subsystem operates in conjunction with a beamsplitter for each said eyewear lens.

3. The eye parallax tracking system of claim 1, wherein: said illumination subsystem comprises a near-infrared laser diode light source producing said beams of light; a focusing optic arranged to inject said beams into each said waveguide, wherein each said injected beam propagates through the respective said waveguide via total internal reflection onto a volume reflection hologram; wherein said each hologram is laminated or imbedded into the respective said waveguide at a position that in use is in front of the respective eye; and wherein in operation said each hologram collimates and redirects the light onto the respective eye.

4. The eye parallax tracking system of claim 1, wherein said imaging subsystem comprises volume reflection holograms laminated to or embedded into each eyewear waveguide; wherein in use each said hologram receives retro-reflected light beam from said illumination subsystem from said eye and refocuses said retro-reflected beam and redirects it inside of said waveguide; wherein each said beam propagates through said waveguide by total internal reflection and exits through a microprojecting lens; wherein said microprojecting lens compensates for aberrations associated with said hologram and forms an image of the first Purkinje point from each eye onto a compact CCD or PSD receiver.

5. The eye parallax tracking system of claim 4 in which said microprojection lens has decentering of its components to compensate for the coma aberrations of said hologram; said lens having two biconic surfaces to compensate for both quadratic and constant astigmatism over the entire field of view of said hologram.

6. The eye parallax tracking system of claim 4, wherein the angular selectivity of said volume reflection hologram restricts the input object cone angle of the Purkinje points imaging subsystem to a full angle of less than or equal to 10 degrees, wherein said microprojection lens has a compact split triplet architecture and can resolve more than 200 positions over a normal eye focusing range, and wherein the imaging subsystem is telecentric in object space.

7. The eye parallax tracking system of claim 1, wherein said volume holograms are recorded using a near-infrared wavelength light source, such that said hologram allows visible light to pass through it substantially unaffected.

8. In combination with the eye parallax tracking system of claim 1, an autofocusing eyewear comprising variable-focus lenses, wherein the system controller gives a driving signal to the variable focus lenses based on said representative quantity.

9. The autofocusing eyewear combination of claim 8, wherein the variable power lenses have a sufficient range of focus to provide sharp imaging of objects located at any distance from 250 mm to infinity for a wearer who has presbyopia.

10. An autofocusing eyewear combination with an eye parallax tracking system, comprising:
  a pair of eyewear with transparent waveguides in each eyewear lens;
  an illumination subsystem arranged to direct a beam of light through said waveguides onto a wearer's eyes;
  a First Purkinje point imaging subsystem for each said lens using light reflected from said eyes through said waveguides;
  a controller operative to calculate from the positions of the First Purkinje points of the wearer's eyes a quantity representative of at least one of the wearer's gaze parallax angle and the distance to an object of interest on which the gaze of the wearer's eyes converges; and
  variable-focus lenses, wherein the system controller gives a driving signal to the variable focus lenses based on said representative quantity;
  wherein the variable power lens is a modified Alvarez lens comprising two components of the form
  $$z = A^* x^* y^2/s^3 + B^* x^3/s^3 + D^* x/s,$$

where z is a thickness of the component, x is a coordinate in a direction perpendicular to z in which the components are relatively movable to vary the power of the lens, y a coordinate in a direction perpendicular to x and z, and A, B, D, and s are coefficients and the absolute values of A, B, D, and s are not all the same for the two components.

11. The autofocusing eyewear combination of claim 10, wherein the modified Alvarez lens achieves optical quality of at least 0.3 contrast at 100 pl/mm over a 40° field of view of 40° in a horizontal plane and 30° in a vertical plane, with respect to a wearer standing upright, and 4 diopters of refocusing power.

12. The autofocusing eyewear combination of claim 10, wherein for at least one eye the variable-power lens is suitable for an emmetropic presbyopic eye, and has one component with A=6, B=1.860846, D=−1.6, and s=25, and the other component with A=−7.034551, B=−2.188646 D=1.6, and s=25.

13. The autofocusing eyewear combination of claim 10, wherein for at least one eye the variable-power lens is suitable for a 3-diopter myopic presbyopic eye, and has one component with A=6, B=1.890742, D=−1.6, and s=25, and the other component with A=−6.962333, B=−2.201143, D=1.6, and s=25.

* * * * *